United States Patent [19]

Utterberg

[11] Patent Number: 5,769,815
[45] Date of Patent: Jun. 23, 1998

[54] BLOOD CHAMBER WITH INTEGRAL PROJECTIONS

[75] Inventor: David S. Utterberg, Seattle, Wash.

[73] Assignee: Medisystems Technology Corporation, Las Vegas, Nev.

[21] Appl. No.: 451,007

[22] Filed: May 25, 1995

[51] Int. Cl.$^6$ ........................................ A61M 5/14
[52] U.S. Cl. .................................. 604/80; 604/4; 210/239
[58] Field of Search ................................. 604/4–7, 80–86, 604/251–255, 213; 55/193, 201; 128/DIG. 13; 210/239, 137, 767

[56] References Cited

U.S. PATENT DOCUMENTS

| | | | |
|---|---|---|---|
| 4,048,995 | 9/1977 | Mittleman | 128/214 R |
| 4,368,118 | 1/1983 | Siposs | 210/136 |
| 4,428,743 | 1/1984 | Heck | 604/4 |
| 4,493,705 | 1/1985 | Gordon et al. | 604/4 X |
| 4,643,713 | 2/1987 | Viitala | 604/4 |
| 4,666,598 | 5/1987 | Heath et al. | 210/239 |
| 4,681,606 | 7/1987 | Swan, Jr. et al. | 604/4 X |
| 5,061,236 | 10/1991 | Sutherland et al. | 604/4 |
| 5,061,365 | 10/1991 | Utterberg | 604/5 X |
| 5,160,332 | 11/1992 | Nomura | 604/4 X |
| 5,328,461 | 7/1994 | Utterberg | 604/80 |
| 5,330,425 | 7/1994 | Utterberg | 604/4 X |
| 5,578,070 | 11/1996 | Utterberg | 604/80 |

FOREIGN PATENT DOCUMENTS

| | | |
|---|---|---|
| 0 183 057 | 10/1985 | European Pat. Off. . |
| 0 568 275 A3 | 11/1993 | European Pat. Off. . |
| 2.164.873 | 8/1973 | France . |
| 040157A/90 | 5/1994 | Italy ........................................ 604/4 X |
| 57-176370 | 10/1982 | Japan . |

*Primary Examiner*—Corrine M. McDermott
*Assistant Examiner*—Chalin Smith
*Attorney, Agent, or Firm*—Gerstman, Ellis & McMillin, Ltd.

[57] ABSTRACT

A plastic blood chamber comprises a chamber-defining wall having a first blood inlet port adjacent to the end of the chamber and a blood outlet port adjacent typically the opposed end of the chamber. The inlet port is positioned in separate, lateral relation with the chamber, and has a conduit extending longitudinally of the chamber from the inlet port toward a central chamber portion in such separate, lateral relation to the chamber. The conduit curves into communication with the chamber in a transverse direction at an inlet position in the central chamber portion. A second portion of the chamber which is laterally opposed to the inlet position of the conduit defines a sloping shoulder to turn lateral blood flow from the conduit gently upwardly to define a gentle, circulatory flow of blood in an upper portion of the chamber. The chamber upper portion has a wall that carries projections to create blood flow eddys that slow the upward motion of bubbles present.

21 Claims, 3 Drawing Sheets

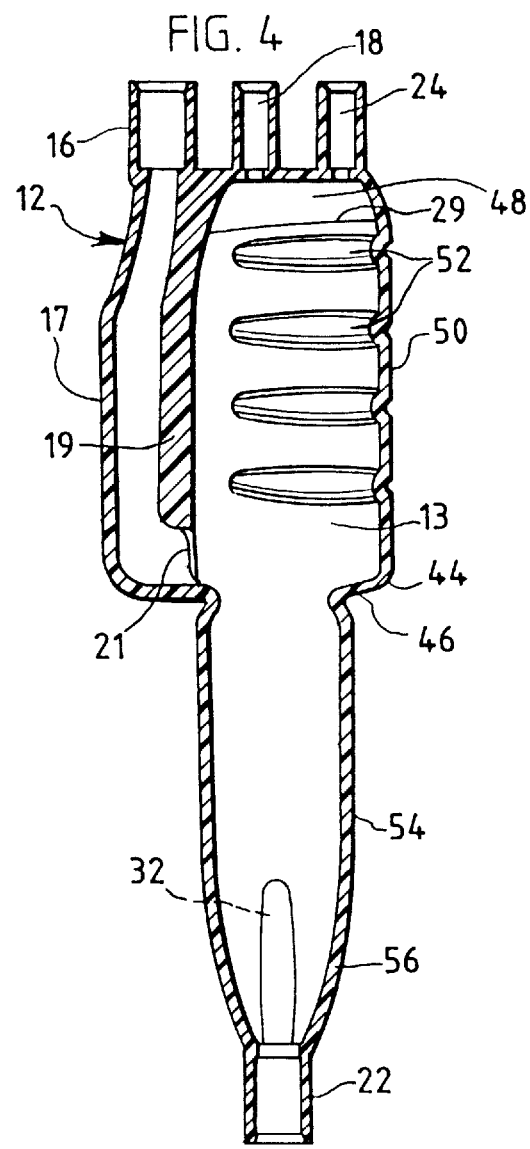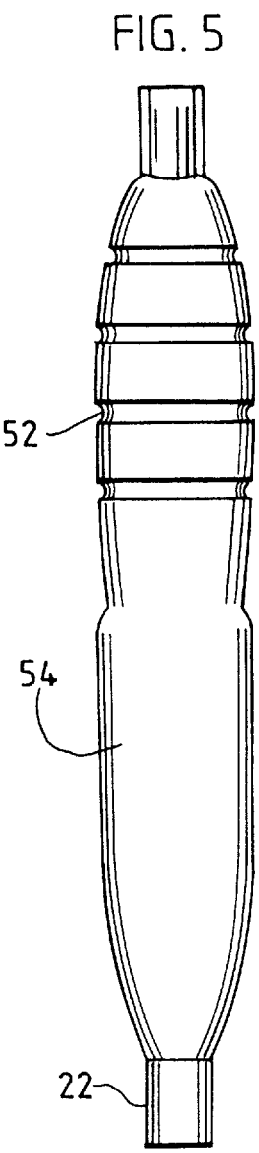

BLOOD CHAMBER WITH INTEGRAL PROJECTIONS

BACKGROUND OF THE INVENTION

In Utterberg U.S. Pat. No. 5,328,461, issued Jul. 12, 1994, a blow molded, venous blood chamber for hemodialysis is disclosed, the disclosures of that patent being incorporated herein by reference.

Blood chambers are used in hemodialysis blood sets, which blood sets convey blood between a patient and a hemodialysis unit. Specifically, the blood chambers, as part of the blood sets, function to remove any gas bubbles that have formed while the blood is outside of a patient. Also, the chambers may be adapted for fitment to a conventional air/foam detector for active monitoring of air in blood exiting the chamber. Also, such blood chambers serve as sites for branching lines which connect to arterial and venous pressure monitors, for example. Similarly, such chambers may provide connection sites for heparin and other parenteral solution administration, as well as an access port for the removing of gas from collected bubbles.

In the above cited patent, several embodiments of blow molded venous blood chambers are shown. One particular embodiment is a blood chamber in which the blood enters the chamber at its midsection in horizontal manner (when the blood chamber is in its position of use), with the result that the blood entering the chamber gently swirls upwardly before being withdrawn from the bottom of the chamber, so that gas bubbles present in the blood are first swept upwardly to join a volume of gas at the top of the chamber above the blood level.

By this invention, an improvement in blood chambers is provided, which gives further assurance that microbubbles of blood are not swept along with the blood being withdrawn from the chamber, passing through the chamber and resulting in undesirable effects on the patient as the blood is returned.

DESCRIPTION OF THE INVENTION

In accordance with this invention, a plastic blood chamber comprises a chamber-defining wall having a first blood inlet port adjacent an end of the chamber and a blood outlet port adjacent an end of the chamber. Typically, the inlet and the outlet ports are positioned at opposite chamber ends, although in some designs they may be positioned at the same end. The inlet port may be positioned in separate, lateral relation with the chamber, while being typically attached thereto as part of a single, integral parison from which the chamber is manufactured by blow molding.

The inlet port has a conduit extending longitudinally along the chamber from the inlet port toward a central chamber portion, the conduit being typically connected with the chamber wall. The conduit curves into flow communication with the chamber in a transverse direction relative to the axis between the chamber ends, at an inlet position in a central chamber portion, spaced from the ends.

A second portion of the chamber, which is laterally opposed to the inlet position of the conduit, may define a sloping or angled surface. The purpose of this sloping surface, which may be curved, is to turn lateral blood flow from the conduit gently upwardly to define a gentle, circulatory flow of blood in an upper portion of the chamber, as described in the previously cited patent.

In accordance with this invention, a chamber upper portion has a wall that carries inwardly or outwardly-extending projections to create blood flow eddys that slow the upward motion of bubbles present in the blood flowing through the chamber. Without wishing to be bound by any theory of operation, it is believed that this facilitates the likelihood that the bubbles will either reach the surface of the blood and join the air space above the blood, or stay by the sidewall near the projection, where, in time, they may coalesce with other bubbles and then rise to the surface. In either case fewer bubbles will be moving so fast in the flow that they can "bounce" off of the underside of the blood level and continue on in the circulatory blood flow, from where they may be sucked into the lower section of the blood chamber and out the outlet along with flowing blood. By means of the projections in accordance with this invention, the amount of gas in bubbles passing through the blood chamber without being caught and retained is reduced.

Preferably, the blood chamber of this invention also defines a lower portion having a circular cross section, and being of sufficient flexibility to permit positioning of the lower portion in an air/foam detector, particularly one of currently conventional design. Such detectors typically require a cylindrical chamber portion to fit onto the measurement heads of the detector. This can be provided by the lower portion.

However, the chamber upper portion may be of non-cylindrical shape, for example oval, being typically of greater cross-sectional area than the cross-sectional area of the preferably cylindrical chamber lower portion.

In another preferred aspect of the invention, the curved surface described above and the inlet portion of the conduit are positioned adjacent to a chamber junction portion between the chamber upper and lower portions.

Also, the projections imposed in the chamber wall in accordance with this invention are preferably linear in shape and transverse to an axis between the chamber ends. Thus, rising blood in the chamber has to cross these linear projections, which tend to create bubble-slowing eddys, so that fewer of the bubbles strike the upper surface of the blood in such a way as to rebound downwardly.

The inwardly extending projections formed in the wall of the blood chamber in accordance with this invention may be used in conjunction with other blood chambers, as well as the one specifically described herein, to achieve a substantially similar improvement.

DESCRIPTION OF THE DRAWINGS

In the drawings.

FIG. 4 is a longitudinal sectional view of the chamber of FIG. 2; and

FIG. 5 is a side elevational view taken from the other side of FIG. 3.

DESCRIPTION OF SPECIFIC EMBODIMENTS

Figure 1:
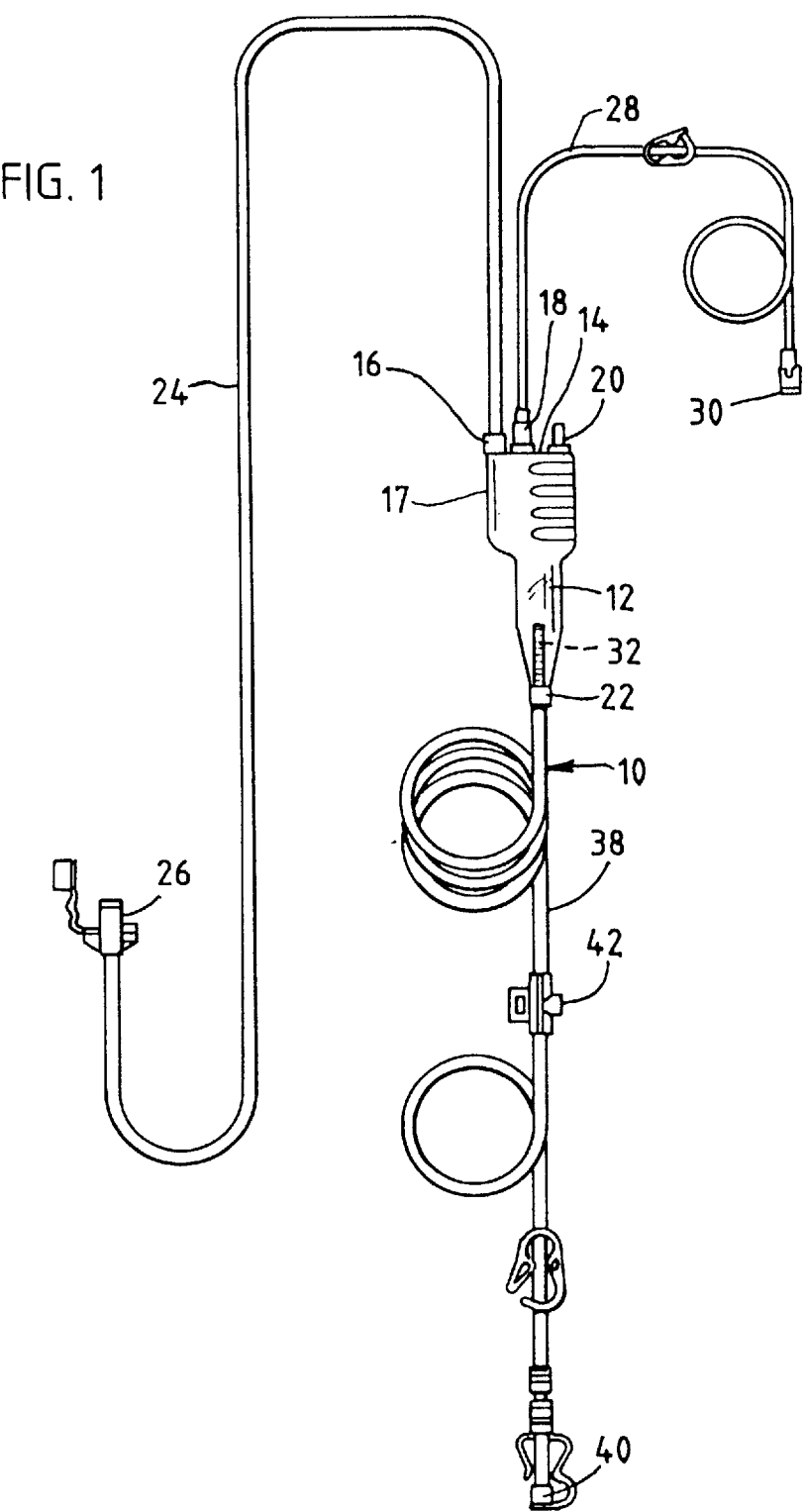
FIG. 1 is a plan view of a venous hemodialysis set which carries a blow molded chamber of this invention.
Figure 2:
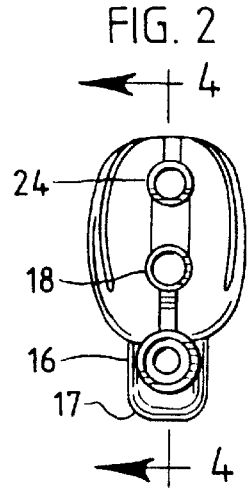
FIG. 2 is a top plan view of the chamber of this invention.
Figure 3:
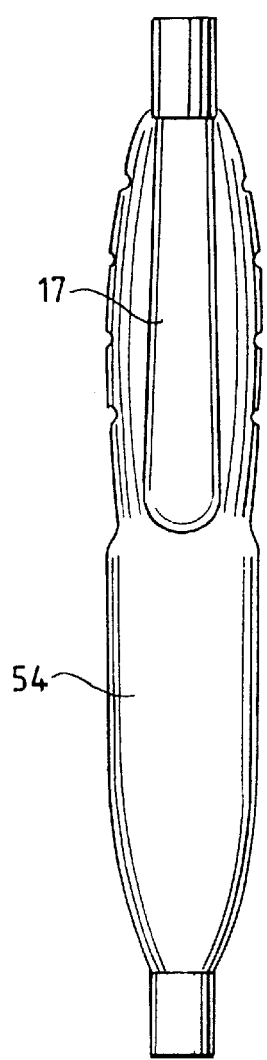
FIG. 3 is a side elevational view of the chamber of FIG. 2.

Referring to the drawings, FIG. 1 shows a venous hemodialysis set 10 which may be generally conventional in design except for the blow-molded plastic chamber 12 of this invention carried in set 10.

Blow molded plastic chamber 12, as shown, comprises a first end 14 defining three separate first access ports 16, 18, 20, communicating with inner chamber 13.

Plastic chamber 12 also defines a second access port 22 at the end opposed to first end 14.

Blow molded venous chamber 12 may be blow molded from a parison of flexible or rigid plastic such as rigid polyvinyl chloride, or poly(ethyleneterephthalate), particularly a glycol-modified variety of the later. Suitable plastic formulations for this purpose are commercially available.

Access port 16 of chamber 12 communicates with flexible tubing 24, with tubing 24 typically being sealed within port 16. Tubing 24 at its other end carries as conventional connector 26, which is adapted for connection with a blood outlet port of a hemodialyzer.

Access port 18 may be connected to pressure monitor tubing 28, which carries at its opposed end a conventional connector 30 for a pressure monitor.

Access port 20 may comprise a conventional needle pierceable partition of resealable elastomer, of a conventional design, for purpose of adding medicine to the flow system, and for removing gas or air from the chamber to raise the blood level 29 therein.

Second access port 22 is shown to carry a tubular plastic filter 32, which may be of a construction similar to that shown in the previously cited patent. Flexible tubing 38 also enters into port 22 within the port at a position outwardly from the plastic filter 32 to retain the plastic filter in a manner discussed in the previous patent. Tubing 38 may be conventionally sealed in its position in second port 22.

The opposed end of tubing 38 defines a conventional connector 40 for connection to a fistula needle, which, in turn, penetrates the fistula of the patient for return of dialyzed blood.

Injection site 42 is also carried on tubing 38, and may be of conventional design.

Access port 16 is shown to be carried on a separate, generally longitudinal conduit 17, made out of the material of the same parison as chamber 12 in its blow molding, being separated from the remainder of chamber 12 by partition line 19 (FIG. 4). Tubular conduit 17 may be approximately cylindrical in shape if desired. Then, tubular conduit 17 communicates with the inner chamber 13 at an inlet position 21, causing blood to flow transversely from conduit 17 into chamber 13. By this means, a third port may be provided to the first end of plastic chamber 12 without undue crowding of the respective ports. Also, other advantages are achieved as described herein.

Referring also to FIGS. 2–5, the blood chamber of this invention is disclosed in detail, comprising a central chamber portion 44 in which inlet position 21 is located, and also defining sloping shoulder 46, which may be curved or straight as desired and at a position laterally opposed to inlet position 21. Thus, the entry of blood through inlet position 21, below blood level 29, causes the blood flow to be turned upwardly by the gentle slope of shoulder 46 to form a circulating blood flow. Any entrained air bubbles will be carried upwardly along with the blood toward the blood surface 29 to join the air or gas space 48.

In accordance with this invention, an upper portion 50 of plastic chamber 12 defines inwardly extending projections 52, which are shown to be linear and circumferential, extending in arcs of approximately 180° about the central axis of chamber 13. Thus, blood moving upwardly as impelled by shoulder 46 will have its flow diverted into eddys that slow the upward motion of bubbles present, but do not stop such upward motion. Thus, the bubbles do not rise to such a rapid degree that they exhibit the "bounce" off of blood level 29 and flow back downwardly again with the downwardly descending blood. Rather, the blood bubbles tend to approach the blood level 29 more slowly, and merge with the air space 48 above blood level 29.

Plastic chamber 12 also defines a lower portion 54 of substantially circular cross section, and typically cylindrical along a major portion of its length, although tapered inwardly at lowermost section 56 if desired, to join with second or outlet port 22. As stated before, this makes it possible for blood chamber 12 to be mounted in a conventional air/foam detector, while its upper portion 50 may be designed to be of substantially oval cross section (not considering the added component of conduit 17) for optimum blood handling, bubble removal, and flow.

Particularly, the blood chamber of this invention is useful at the relatively high blood flow rates which are becoming more common in hemodialysis, while still exhibiting good bubble removal characteristics.

The preferably linear, circumferential indentations of this invention may be used on other designs of blood chambers, as well as the specific design of chamber shown herein.

The chamber of this invention may be resilient or flexible, although it is typically of sufficient stiffness to support its shape. The purpose of the resilience is to permit intimate contact and good functioning of the blood chamber in the air/foam detector, so the typically desired amount of resilience or flexibility is relatively small.

Chamber 12 may be about 136–137 mm. in length, for example.

The above has been offered for illustrative purposes only, and is not intended to limit the scope of the invention of this application, which is as defined in the claims below.

That which is claimed:

1. A blood chamber which comprises a chamber-defining wall and an upper end, a lower end, a blood flow chamber inlet, and a blood flow outlet, said blood flow chamber inlet being spaced from the upper end whereby blood can enter said chamber below the upper surface of blood in the chamber, said chamber-defining wall having an upper portion that carries a plurality of projections, said projections being longitudinally spaced in the direction of a chamber longitudinal axis and positioned transversely to said axis, to create blood flow eddies that slow the upward motion of bubbles present.

2. The chamber of claim 1 in which a plurality of said projections are linear and positioned circumferentially in said chamber wall about said axis between the chamber ends.

3. The blood chamber of claim 1 in which said chamber defines a resilient, lower portion of substantially circular cross section to permit positioning of said lower portion in an air/foam detector.

4. The blood chamber of claim 3 in which said chamber upper portion is of non-cylindrical shape, and is of greater cross-sectional area than said chamber lower portion.

5. The blood chamber of claim 1 in which the blood outlet is positioned adjacent said lower end.

6. The chamber of claim 5 in which said projections are linear.

7. The chamber of claim 6, in which said projections extend inwardly.

8. A plastic blood chamber which comprises a chamber defining wall having a blood inlet port adjacent an end of the chamber and a blood outlet port communicating with the chamber, said inlet port being positioned in separate, lateral relation with said chamber, and having a conduit extending longitudinally along said chamber from the inlet port toward a central chamber portion in said separate, lateral relation to the chamber, said conduit curving into communication with said chamber in a transverse direction to a chamber longitudinal axis at an inlet position in said central chamber portion, a second portion of said chamber laterally opposed to the inlet position of said conduit defining a sloping surface to turn lateral blood flow from said conduit gently upwardly to define a gentle, circulatory flow of blood in an upper portion of said chamber, said chamber upper portion having a wall that carries a plurality of projections, said projections being longitudinally spaced in the direction of said axis and positioned transversely to said axis, to create blood flow eddies that slow the upward motion of bubbles present.

9. The chamber of claim 8, comprising part of a venous set for hemodialysis.

10. The chamber of claim 8 in which said projections are linear.

11. The chamber of claim 8 in which said inlet port and said outlet port are positioned at opposed chamber ends.

12. The chamber of claim 8 in which said at least one projection is inwardly extending.

13. The blood chamber of claim 8 in which said chamber defines a flexible, lower portion of substantially circular cross section, to permit positioning of said lower portion in an air/foam detector.

14. The blood chamber of claim 13 in which said chamber upper portion is of non-cylindrical shape, and is of greater cross-sectional area than said chamber lower portion.

15. The blood chamber of claim 14 in which said sloping surface and said inlet position of the conduit are positioned adjacent to a chamber junction portion between said chamber upper and lower portions.

16. A plastic blood chamber which comprises a chamber-defining wall having a first blood inlet port adjacent an end of the chamber and a blood outlet port communicating with of the chamber, said inlet port being positioned in separate, lateral relation with said chamber and having a conduit extending longitudinally along said chamber from the inlet port toward a central chamber portion in said separate, lateral relation to the chamber, said conduit curving into communication with said chamber, in a transverse direction to a chamber longitudinal axis, at an inlet position in said central chamber portion, a second portion of said chamber laterally opposed to the inlet portion of said conduit defining a sloping surface to turn lateral blood flow from said conduit gently upwardly to define a gentle, circulatory flow of blood in an upper portion of said chamber, said chamber upper portion having a wall that carries a plurality of projections, said projections being longitudinally spaced in the direction of said axis and positioned transversely to said axis, to create blood flow eddies that slow the upward motion of bubbles present; said chamber defining a flexible, lower portion of substantially circular cross section to permit positioning of said lower portion in an air/foam detector, said projections being substantially linear, and positioned transversely to an axis between the chamber ends.

17. The blood chamber of claim 16 in which said inlet port and said outlet port are positioned at opposed chamber ends.

18. The blood chamber of claim 16 in which said projections extend inwardly.

19. The blood chamber of claim 16 in which said chamber upper portion is of non-cylindrical shape, and is of greater cross-sectional area than said chamber lower portion.

20. The chamber of claim 19 in which said inlet port and said outlet port are positioned at opposed chamber ends.

21. The blood chamber of claim 20 in which said sloping surface and said inlet position of the conduit are positioned adjacent to a chamber junction portion between said chamber upper and lower portions.

\* \* \* \* \*